United States Patent
Demi et al.

(10) Patent No.: US 8,131,032 B2
(45) Date of Patent: Mar. 6, 2012

(54) APPARATUS FOR AUTOMATIC DETECTION OF LUMEN-INTIMA AND MEDIA-ADVENTITIA INTERFACES IN A BLOOD VESSEL

(75) Inventors: Marcello Demi, Montescudaio (IT); Vincenzo Gemignani, Torre del Lago Puccini (IT); Francesco Faita, La Spezia (IT)

(73) Assignees: CNR—Consiglio Nazionale Delle Ricerche, Rome (IT); Esaōte S.P.A., Frienze (IT)

( * ) Notice: Subject to any disclaimer, the term of this patent is extended or adjusted under 35 U.S.C. 154(b) by 1133 days.

(21) Appl. No.: 11/845,844

(22) Filed: Aug. 28, 2007

(65) Prior Publication Data

US 2008/0051658 A1  Feb. 28, 2008

(30) Foreign Application Priority Data

Aug. 28, 2006  (IT) .............................. PI2006A000105

(51) Int. Cl.
   *G06K 9/00* (2006.01)
(52) U.S. Cl. ........ 382/128; 382/100; 382/131; 382/132; 382/168; 382/171; 600/407; 600/437; 600/443
(58) Field of Classification Search .................. 382/100, 382/128, 131, 132; 600/407, 437, 443
   See application file for complete search history.

(56) References Cited

U.S. PATENT DOCUMENTS 6,835,177 B2 * 12/2004 Fritz et al. .................... 600/443
2003/0199762 A1 * 10/2003 Fritz et al. .................... 600/437

OTHER PUBLICATIONS

"A Multiscale Dynamic Programming Procedure for Boundary Detection in Ultrasonic Artery Images" by Q. Liang, I. Wendelhag, J. Wikstrand, and T. Gustavsson. IEEE Trans. Med. Imag. vol. 19, No. 2, (Feb. 2000).*

* cited by examiner

*Primary Examiner* — Tse Chen
*Assistant Examiner* — Jason Ip
(74) *Attorney, Agent, or Firm* — Dennison, Schultz & MacDonald

(57) ABSTRACT

An apparatus for defining the lumen-intima interface and media-adventitia interface of a blood vessel, for example the carotid artery, comprises a means for acquisition of a two-dimensional representation, generated by an ultrasonographic machine, of a longitudinal or transverse cross section of the vessel. In the two-dimensional representation a region of interest (ROI) is defined comprising the interface lumen-intima and the interface media-adventitia of the vessel. In the ROI N search paths are then defined from the inside to the outside of the vessel. Along each search path i the values f(n, m) are taken of the two-dimensional representation, which are then subject to filtering obtaining filtered values. This allows retrieving discontinuity points of the two-dimensional representation and then localizing the lumen-intima and media-adventitia interfaces through further logical operations.

15 Claims, 3 Drawing Sheets

APPARATUS FOR AUTOMATIC DETECTION OF LUMEN-INTIMA AND MEDIA-ADVENTITIA INTERFACES IN A BLOOD VESSEL

FIELD OF THE INVENTION

The present invention relates to an apparatus for automatic detection of lumen-intima and media-adventitia interfaces in a blood vessel by analysing a two-dimensional representation thereof. In particular, but not exclusively, the position of such interfaces can be used for determining the intima+media thickness and the diameter of the blood vessel.

DESCRIPTION OF THE PRIOR ART

Vascular screening has achieved in the last years a big importance for prevention and early diagnosis of cardiovascular diseases such as hypertension, arteriosclerosis, infarction, cerebrovascular accident and ischemia.

In particular, vascular stiffness and average intimal thickening are very important parameters for determining the cardiovascular risk. Such parameters can be evaluated in an effective way by easy diagnostic analysis such as sonography, i.e. a relatively not much expensive, not invasive and not ionizing technique.

The step of determining such parameters is essentially based on defining the lumen-intima and media-adventitia interfaces of an examined vessel.

Presently different methods have been developed, manual automatic, for determining such interfaces.

However, the methods based on manual measurements are not much reliable owing to measurement errors and repeatability. Furthermore, they require an expert operator and are extremely expensive versus the time required for carrying out the measurement.

In U.S. Pat. Nos. 6,132,373 and 6,817,982, for example, methods are described to determine the lumen-intima and media-adventitia interfaces through the analysis of values of luminance, i.e. brightness due to each single pixel of digital images obtained with sonographic techniques.

Both methods are based on distinguishing the various structures of the vessel and exploiting the knowledge for localizing the lumen-intima and media-adventitia interfaces. In both patent specifications, furthermore, the interfaces are detected only for calculating the intima+media thickness and not the diameter of the vessel. Differently from these two patent specifications, it is desirable to detect directly the interfaces sought only analysing mathematical derivative functions starting from a two-dimensional representation.

Other authors have proposed alternative methods for characterizing a blood vessel. However none of these uses algorithms and mathematical operators like the present invention.

For example, Gutierrez et al. "Automatic measurement of carotid diameter and wall thickness in ultrasound images" (*Computers in Cardiology*, 2002, vol. 29, pp. 359-362) use an approach based on an active contour technique where the external forces are proportional to the local gradient of the image obtained from a multiscale analysis.

Cheng et al. "Using snakes to detect the intimal and adventitial layers of the common carotid artery wall in sonographic images", (*Computers Methods and Programs in Biomedicine*, vol. 67, 2002, pp. 27-37) use an approach based on the "snakes" model proposed by Cohen et al. described in the article "On active contour models and ballons" (Computer Vision Graphics Image Processing and Image Understanding, vol. 53, No. 2, 1991, pp. 211-218) suitably modified and with the addition of different optimized constraints for application on sonographic images.

Liang et al. "A multiscale dynamic programming procedure for boundary detection in ultrasonic artery images" (*IEEE Transactions on Medical Imaging*, vol. 19, No. 2, 2000, pp. 127-142) use of dynamic programming techniques integrating in a single measure the values of luminance of the image and of intensity of the gradient of the image to obtain a correct position of the lumen-intima and media-adventitia interfaces in a semiautomatic way.

Golematti et al. "Carotid artery wall motion estimated by B-mode ultrasound using region tracking and block matching" (*Ultrasound in Medicine & Biology*, vol. 29, No. 3, 2003, pp. 387-399) use an approach based on "region tracking" and "block matching" techniques for estimating the motion of the walls of a vessel without distinguishing the position of the lumen-intima and media-adventitia interfaces.

Finally, P. J. Brands et al., "An integrated system for non-invasive assessment of vessel wall and hemodynamic properties of large arteries by means of ultrasound", (*European Journal of Ultrasound*, vol. 9, 1999, pp. 257-266) carry out an analysis of only the visible lines of the radiofrequency signal obtained with sonographic techniques (M-mode) by applying to them a "window tracking" algorithm

SUMMARY OF THE INVENTION

It is then a feature of the present invention to provide an apparatus for automatic detection of lumen-intima and media-adventitia interfaces in a blood vessel that avoids the drawbacks of the methods of the prior art.

It is another feature of the present invention to provide such an apparatus that allows calculating the intima+media thickness of a blood vessel.

It is also an feature of the present invention to provide such an apparatus for monitoring the variation of the intima+media thickness during a cardiac cycle.

It is to further particular feature of the present invention to provide an apparatus for automatic detection of lumen-intima and media-adventitia interfaces that allows also calculating the diameter of a blood vessel and monitoring its variation during the cardiac cycle.

These and other features are accomplished with one exemplary apparatus for automatic detection of lumen-intima and media-adventitia interfaces in a blood vessel comprising:
- acquisition means of a two-dimensional cross sectional representation of said blood vessel, said two-dimensional representation being obtained as a grey level image, in said image a region of interest (ROI) being defined that includes said lumen-intima interface and said media-adventitia interface of said vessel, said region of interest consisting of a grey level map f(n, m) of said representation, being n and m the coordinates of each pixel of said two-dimensional representation whose characteristic is that it comprises:
- means for executing, along a search path (i) (with i=1 ... N) in said region of interest and substantially orthogonal to the wall of the vessel, the following operations:
  - indication of discontinuity points by means of filtering the values f(n, m) along the path (i) and localization of said points,
  - definition along said path of a first discontinuity point $P_1(i)$ having contrast greater or equal to a first reference value $S_1$ and definition of a second discontinuity point $P_2(i)$ having contrast greater or equal to a second reference value $S_2$,
  - repeating the acquisition, filtering and definition for a number N of rectilinear search paths in the above described region of interest (ROI):
  - detection of lumen-intima interface by means of interpolation of a set α of points $P_1(i)$ of the different search paths (i), detection of the media-adventitia interface by means of interpolation of a set β of said points $P_2(i)$ of the different search paths (i).

In particular, if the cross section of the vessel is a longitudinal cross section, the search paths can be parallel and equidistant, whereas if the cross section of the vessel is a transverse cross section, the rectilinear search paths may have radial direction with respect to the centre of the vessel and result rotated as multiples of a fixed angle.

Advantageously, first discontinuity point $P_1(i)$ corresponds to the discontinuity point nearest to the centre C of the blood vessel having contrast greater or equal to reference value $S_1$, and second discontinuity point $P_2(i)$ is obtained starting from $P_1(i)$ proceeding outwards of the vessel, along relative i search path.

In particular, the region of interest (ROI) can be a rectangular matrix, consisting of R lines and C columns, containing the values f(n, m) of the two-dimensional representation, being n and m the coordinates of each pixel.

Advantageously, the two-dimensional representation is selected from the group comprised of:
 a B-mode representation obtained by means of a sonographic apparatus;
 a set of envelope curves of the RF signals of a sonographic apparatus.

In particular, the step of indication and detection of the discontinuity points can be made by defining local peaks of the response of the first order absolute central moment operator calculated as:

$$e(n,m)=\Sigma\Sigma_{(k_2,l_2)\in\Theta_2}|[\Sigma\Sigma_{(k_1,l_1)\in\Theta_1}f(n-k_1,m-l_1)w(k_1,l_1,r_1)]-f(n-k_2,m-l_2)|w(k_2,l_2,r_2)$$

being $\Theta_1$ and $\Theta_2$ two circular domains having radius $r_1$ and $r_2$ respectively, defined as:

$$\Theta i=\{(k_i,l_i)\in Z^2:\sqrt{k_i^2+l_i^2}\leq r_i\},$$

where Z represents a set of the whole numbers and $(k_i, l_i)$ are the coordinates of a generic point with respect to a Cartesian plane with origin in (n, m), and wherein $w(k_1, l_1, r_1)$ is a weight function with unitary summation on a domain $\Theta_1$ and $w(k_2, l_2, r_2)$ is a weight function with unitary summation on a domain $\Theta_2$.

In this case, the contrast of a discontinuity point coincides with the value of the absolute central moment of the first order calculated in the point.

Alternatively, the above described step of indication and detection of the discontinuity points can be carried out through the search of local peaks of the response of the Gradient of Gaussian operator calculated as:

$$G(n,m)=\sqrt{\left(\sum\sum_{(k,l)\in\Theta}f(n-k,m-l)\cdot g_x(k,l)\right)^2+\left(\sum\sum_{(k,l)\in\Theta}f(n-k,m-l)\cdot g_y(k,l)\right)^2}$$

where $g_x(k, l)$ and $g_y(k, l)$ show the derivatives of a Gaussian function with respect to directions x and y.

In this case, the contrast value at the discontinuity point coincides with the value itself of the gradient of Gaussian calculated in the point.

Alternatively, the above described step of indication and detection of the discontinuity points can be carried out through the search of zero crossings of the response of the Laplacian of Gaussian operator calculated as:

$$L(n,m)=\Sigma\Sigma_{(k,l)\in\Theta}f(n-k,m-l)\cdot(g_{xx}(k,l)+g_{yy}(k,l))$$

where $g_{xx}(k, l)$ and $g_{yy}(k, l)$ show the second derivatives of a Gaussian function with respect to directions x and y.

In this case, the contrast value at the discontinuity point coincides with the value of the slope at the zero crossing of the Laplacian of Gaussian.

In particular, the above described values of reference $S_1$ and $S_2$ can be calculated for each search path (i) respectively as:

$$S_1=TH_1\cdot C_{MAX}$$

and $$S_2=TH_2\cdot C_1,$$

where
 $C_{MAX}$ is the maximum contrast value of a discontinuity point of the i search path,
 $C_1$ is the contrast value at point $P_1(i)$,
 $TH_1$ is a constant having value comprised between 0 and 1 and $TH_2$ is a constant having value close to 1.

Advantageously, a step is provided of rejecting points $P_1(i)$ to which no points $P_2(i)$ correspond, i.e. for which the search of the corresponding points $P_2(i)$ fails. This way, the "outliers", i.e. any abnormal measurements, are eliminated from the calculus of the interface.

In particular, for eliminating the outliers the following operations can be provided:
 measuring the distance of points $P_1(i)$ belonging to a set α selected from the calculated lumen-intima interface,
 rejecting certain points $P_1(i)$ belonging to a set α of those points having a distance, from the calculated lumen-intima interface, greater than a determined constant DLI, forming a new set α' of points $P_1(i)$,
 defining the lumen-intima interface by means of interpolation of new set α',
 iteration of the previous steps up to eliminating further possible points $P_1(i)$ of a set α' having a distance, from the calculated lumen-intima interface, greater than DLI.

Similarly, in the calculus of the media-adventitia interface the following operations can be provided:
 measuring the distance of points $P_2(i)$ belonging to a set β from the media-adventitia calculated interface,
 rejecting points $P_2(i)$ having a distance, from the media-adventitia calculated interface, greater than a constant DMA, forming a new set β',
 defining the media-adventitia interface by means of interpolation of new set β' of points $P_2(i)$,
 iteration of the previous steps up to eliminating possible further points $P_2(i)$ having a distance, from the media-adventitia calculated interface, greater than DMA.

In particular, the interpolation of a set α of points $P_1(i)$ and of a set β of points $P_2(i)$ is selected from the group comprised of:
 linear interpolation,
 linear alternated interpolation,
 interpolation of an order higher than the first.

The calculus of the distance between the generic point $P_1(i)$ and the interface depends on the type of interpolation used. For example, in case of linear interpolation the distance between a point and a straight line can be used. Instead, in case of interpolation with a curve γ, the minimum distance can be used between a point $P_1(i)$ and the points of γ.

Similar steps can be done for calculating the media-adventitia interface.

Advantageously, a further step can be provided of calculus of the intima+media thickness as a distance between the above described lumen-intima and media-adventitia interfaces.

In particular, the intima+media thickness can be calculated as a succession of two-dimensional representations corresponding to one or more cardiac cycles. This way, it is possible to monitor the variation of the intima+media thickness during such cardiac cycles.

The detection of lumen-intima and media-adventitia interfaces can be used to calculate the diameter of a vessel. In fact, if the lumen-intima interface, or the media-adventitia interface, is measured at two opposite sides of the cross section of the vessel, the distance between the two opposite interfaces lumen-intima, or media-adventitia, corresponds to the inner diameter of the vessel same.

Advantageously, the inner diameter of the vessel is calculated as a succession of two-dimensional representations corresponding to one or more cardiac cycles.

In particular, the algorithm used for calculating the intima+media thickness depends in general on the type of interpolation used in the calculus of the interface.

More in detail, in case of linear interpolation, the lumen-intima and media-adventitia interfaces are defined as two line segments and the intima+media thickness can be calculated in the following way:
    calculus of the central point of one of the two segments,
    calculus of the distance between this central point and the second segment.

In case of interpolation with a curve, the lumen-intima and media-adventitia interfaces are defined as two segments of a curve and the intima+media thickness can be calculated in the following way:
    calculus of a line central to the two curved segments,
    computing N equidistant points on the above described central line,
    calculus of the average of the distance between N points of one curve and the corresponding N points of the other curve obtained as intersection of N line segments orthogonal to the central line exiting from the N equidistant points determined on the same central line.

According to another aspect of the invention, a ultrasonographic machine comprises an apparatus as above described.

BRIEF DESCRIPTION OF THE DRAWINGS

The invention will be made clearer with the following description of an exemplary embodiment thereof, exemplifying but not limitative, with reference to the attached drawings wherein:

With reference to FIG. 1, an apparatus 100, according to the invention, can comprise an ultrasonographic machine and a computer, comprising each a respective hardware case and a monitor, and diagrammatically indicated as a whole with reference numbers 50, 60, respectively. Since the ultrasonographic machine and the computer are machines that are well known to a person with ordinary skill in the art, they do not require further description in detail. The ultrasonographic machine 50 comprises an ultrasound acquisition means 40 for acquiring a two-dimensional representation 10 of a body part of a patient.

Figure 1:
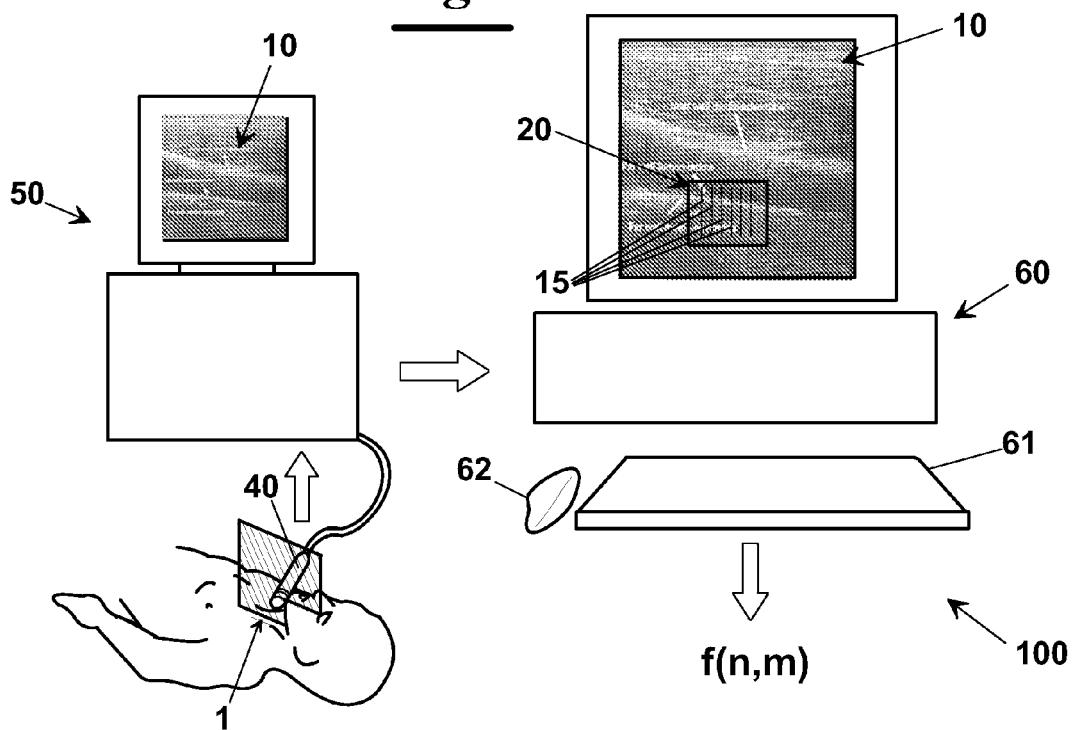
FIG. 1 shows diagrammatically a possible exemplary embodiment of the apparatus, according to the invention, for automatic detection of lumen-intima and media-adventitia interfaces in a blood vessel.

For defining a lumen-intima interface 11 and a media-adventitia interface 12 of a blood vessel 1 of the patient, for example the carotid artery, the ultrasound acquisition means 40, for acquiring a two-dimensional representation 10 of a cross section of vessel 1. The two-dimensional representation 10 can be a B-mode representation generated by ultrasonographic machine 50. Alternatively, the two-dimensional representation 10 can be defined by envelope curves of the RF signals of a sonographic apparatus.

The cross section of vessel 1 can be a longitudinal cross section, as shown in FIG. 1, obtained through a sonographic linear probe 40 by means of non-invasive analysis, or alternatively, a transverse cross section (FIG. 4) obtained by means of a sonographic intravascular probe, not shown in the figures.

Figure 2:
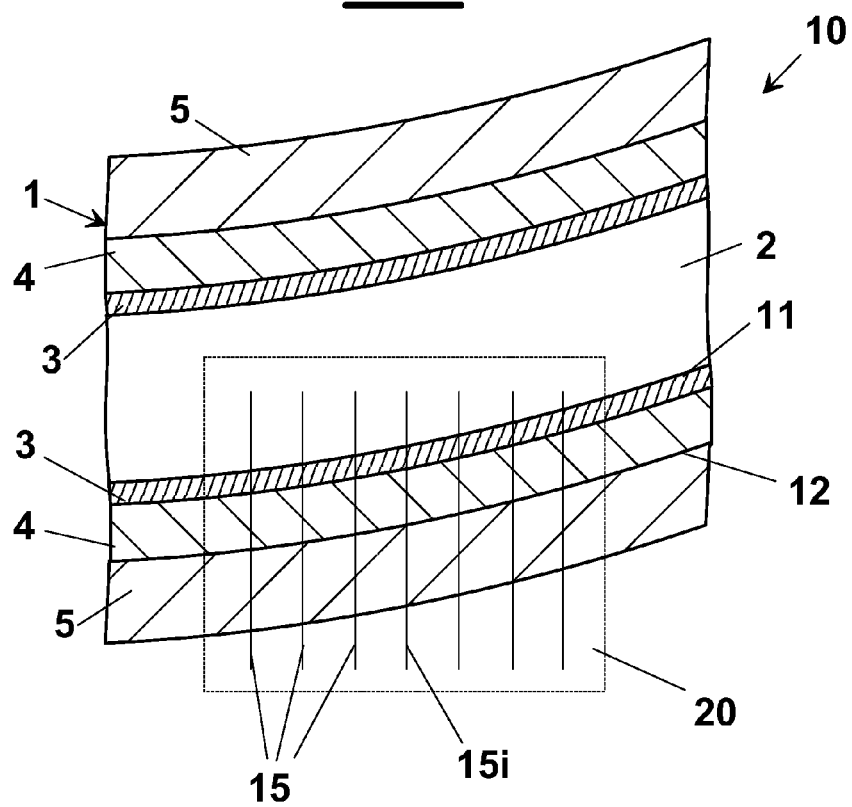
FIG. 2 shows diagrammatically a longitudinal cross sectional view of a blood vessel examined with the apparatus of FIG. 1, FIGS. 3A and 3B show graphical charts of the values of the two-dimensional representation and the response of a passband filter along a search path.
Figure 4:
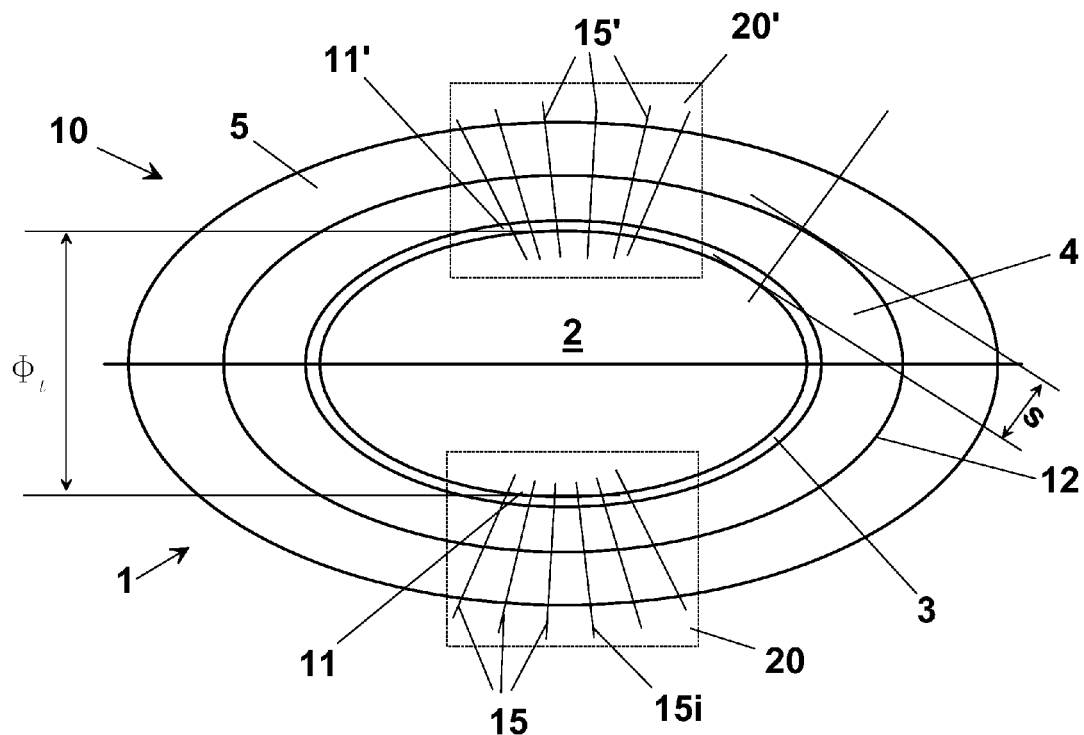
FIG. 4 shows diagrammatically a transverse cross sectional view of a blood vessel examined with the apparatus of FIG. 1.

In FIGS. 2 and 4 respectively a longitudinal cross sectional and a transverse cross sectional view of vessel 1 are diagrammatically shown. In both cases three different concentric overlapping layers are shown forming vessel 1 and precisely an inner layer, which is called intima 3 and defines the channel 2 of vessel 1, an intermediate layer, called media 4, and an outer layer called adventitia 5.

The two-dimensional representation 10 is then transmitted, by means of an analog or digital video output connection, to execution means 60 for being computed by a specific algorithm. In particular, the execution means 60 have peripheral devices, such as a keyboard 61 and a mouse 62, which allow a user to define, in a manual or semi-automatic way, in the two-dimensional representation 10, a region of interest (ROI) 20 comprising lumen-intima interface 11 and media-adventitia interface 12 of vessel 1. The region of interest 20 can be a rectangular matrix, consisting of R lines and C columns, containing the values of the grey level map $f(n, m)$ of the representation. In ROI 20 N search paths 15 are then defined. These are rectilinear segments going from the inside to the outside of vessel 1. In the case of the transverse cross sectional view (FIG. 4) the segments 15 may have a radial direction with respect to the center of vessel 1 for being then rotated for multiples of a fixed angle. In the case of longitudinal cross section (FIG. 2), instead, such segments 15 can be parallel and equidistant and arranged on directions substantially orthogonal to the walls of vessel 1. Such paths 15 can correspond to some of the columns or the lines of ROI 20 when this is a rectangular matrix.

Figure 3A:
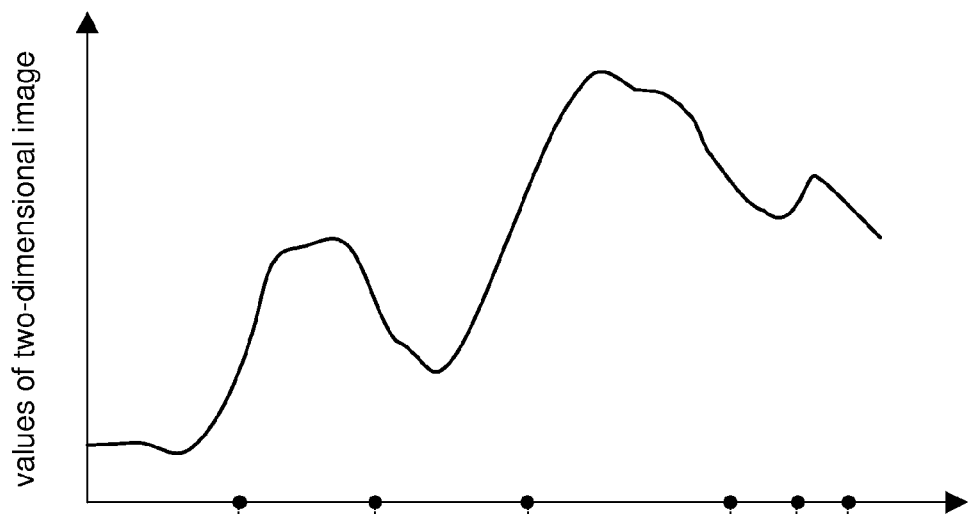
Figure 3B:
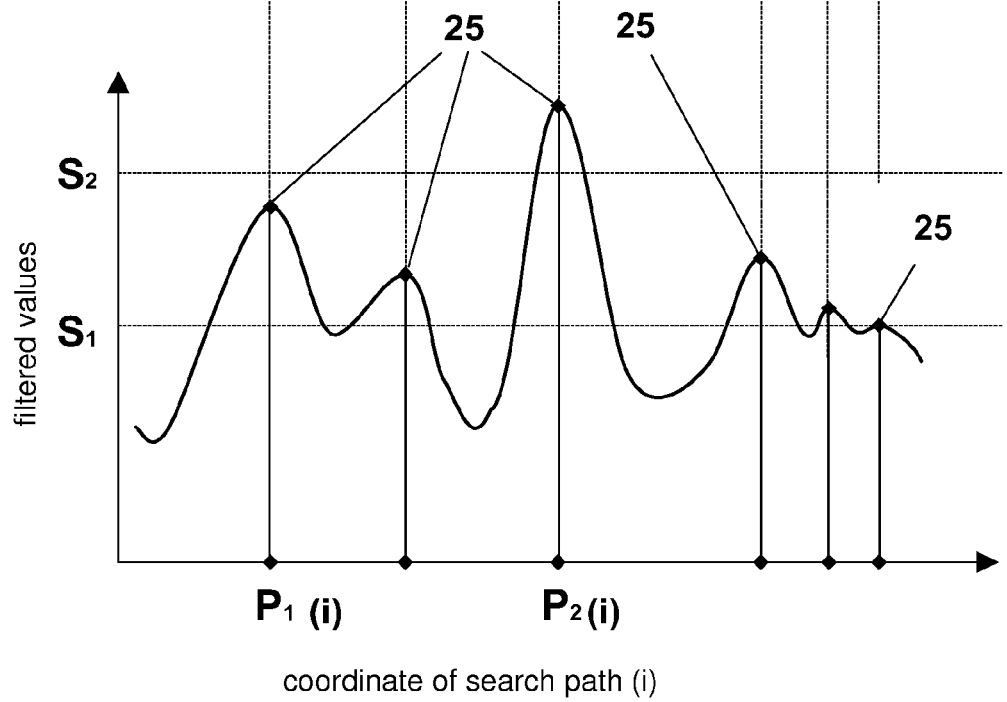

Along each search path $15i$ the values $f(n, m)$ of the two-dimensional representation are taken, graphically shown in FIG. 3A. Such values $f(n, m)$ are, then, subject to a step of filtering, for obtaining filtered values shown graphically in FIG. 3B. This highlights discontinuity points 25 of two-dimensional representation 10.

For example, a search of discontinuity points 25 can be carried out by searching a local maximum of filtered data, resulting from a step of filtering the data carried out with a pass band filter. The filter can be a generalization of the absolute moment of the first order:

DESCRIPTION OF PREFERRED EXEMPLARY EMBODIMENTS

With reference to FIG. 1, an apparatus 100, according to the invention, for defining a lumen-intima interface 11 and a media-adventitia interface 12 of a blood vessel 1, for example the carotid artery, comprises means 40 of acquisition of a two-dimensional representation 10 of a cross section of vessel 1. The two-dimensional representation 10 can be a B-mode representation generated by a ultrasonographic machine 50. Alternatively, the two-dimensional representation 10 can be defined by envelope curves of the RF signals of a sonographic apparatus.

The cross section of vessel 1 can be longitudinal, as shown in FIG. 1, obtained through a sonographic linear probe 40 by means of not invasive analysis, or alternatively, a cross sectional view (FIG. 4) obtained by means of a sonographic intravascular probe, solution not shown in the figures.

In FIGS. 2 and 4 respectively a longitudinal sectional and a cross sectional view of vessel 1 are diagrammatically shown. In both cases three different concentric overlapping layers are shown forming vessel 1 and precisely an inner layer, called intima 3, an intermediate layer, said media 4, and an outer layer called adventitia 5.

The two-dimensional representation 10 is then given by means of a analog or digital video output to execution means 60 for being computed by a specific algorithm. In particular, the means for execution 60 have peripheral devices, such as a keyboard 61 and a mouse 62, which allow to define, in a manual or semi-automatic way, in the two-dimensional representation 10, a region of interest (ROI) 20 comprising lumen-intima interface 11 and media-adventitia interface 12 of vessel 1. The region of interest 20 can be a rectangular matrix, consisting of R lines and C columns, containing the values of the grey level map f(n, m) of the representation. In ROI 20 are then defined N search paths 15. These are rectilinear segments going from the inside to the outside of vessel 1. In case of the cross sectional view (FIG. 4) the segments 15 may have a radial direction with respect to the centre of vessel 1 for being then rotated for multiples of a fixed angle. In case of longitudinal cross section (FIG. 2), instead, such segments 15 can be parallel and equidistant and arranged on directions substantially orthogonal to the walls of vessel 1. Such paths 15 can correspond to some of the columns or the lines of ROI 20 when this is a rectangular matrix.

Along each search path 15$i$ the values f(n, m) of the two-dimensional representation are taken, graphically shown in FIG. 3A. Such values f(n, m) are, then, subject to a step of filtering obtaining filtered values shown graphically in FIG. 3B. This enhances discontinuity points 25 of two-dimensional representation 10.

For example, the search of the discontinuity points 25 can be carried out by searching a local maximum of the resulting data of a step of filtering the data carried out with a pass band filter. The filter can be a generalization of the absolute moment of the first order:

$$e(n,m) = \Sigma\Sigma_{(k_2,l_2)\in\Theta_2} |[\Sigma\Sigma_{(k_1,l_1)\in\Theta_1} f(n-k_1,m-l_1)w(k_1,l_1,r_1)] - f(n-k_2,m-l_2)|w(k_2,l_2,r_2)$$

or alternatively, the modulus of the gradient of Gaussian:

$$G(n,m) = \sqrt{\left(\sum\sum_{(k,l)\in\Theta} f(n-k, m-l) \cdot g_x(k,l)\right)^2 + \left(\sum\sum_{(k,l)\in\Theta} f(n-k, m-l) \cdot g_y(k,l)\right)^2}$$

Once defined the discontinuity points 25, the relative value of the contrast is calculated corresponding to the value of the absolute moment of the first order, or the gradient of Gaussian, depending on the filter used for their definition.

Alternatively, the search of the discontinuity points 25 can be carried out by searching any zero crossings of the result of a filtering operation of the data, carried out with a second order derivative filter. The filter can be a Laplacian of Gaussian:

$$L(n,m) = \Sigma\Sigma_{(k,l)\in\Theta} f(n-k,m-l) \cdot (g_{xx}(k,l) + g_{yy}(k,l))$$

Once defined, the discontinuity points 25, the relative value of the contrast is calculated corresponding to the value of the slope at the zero crossing.

Once detected all the discontinuity points 25 for each search path 15$i$ and calculated the corresponding values of contrast, two points $P_1(i)$ and $P_2(i)$ are selected.

In particular, $P_1(i)$ is the innermost discontinuity point 25 in vessel 1 and is defined by searching a discontinuity point 25 having a contrast greater or equal to reference value $S_1$. Point $P_2(i)$ is searched along the same search path 15$i$ starting from $P_1(i)$ and proceeding outwards of vessel 1 up to retrieving a first discontinuity point 25 having contrast greater or equal to a second reference value $S_2$.

The values $S_1$ and $S_2$ can be two predetermined constants. For example $S_1$ can be calculated for each search path 15$i$ as a product between maximum value ($C_{MAX}$) of the contrast of a discontinuity point 25 of the search path and a constant $TH_1$ having a value comprised between 0 and 1. $S_2$ can instead be calculated for each search path 15$i$ as the product between value $C_1$ of the contrast at point $P_1(i)$ and a constant $TH_2$ having a value close to 1.

Figure 5:
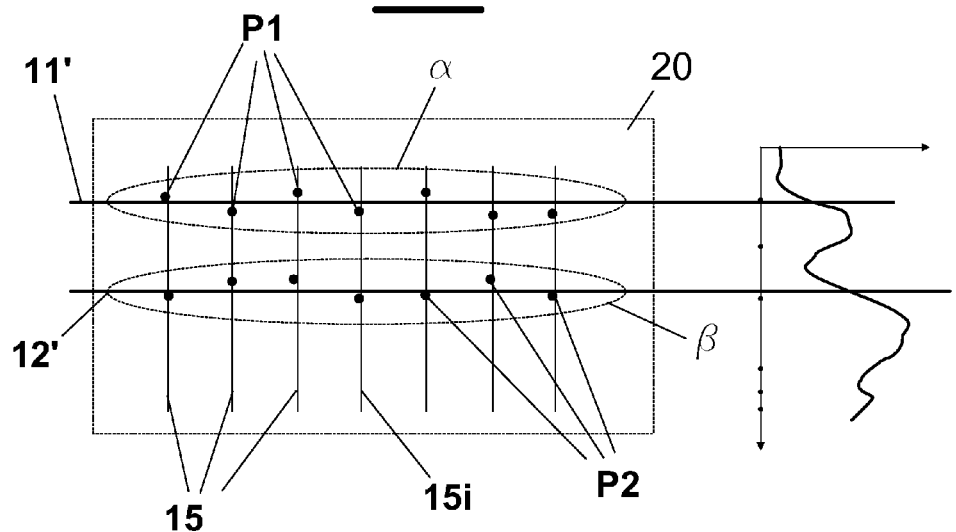
FIG. 5 shows graphically in detail graphical interpolation steps of data relative to a blood vessel through which the detection of the lumen-intima and media-adventitia interfaces is carried out.

From an analysis of the N search paths, thus, two sets ($\alpha$ and $\beta$) of points $P_1(i)$ and $P_2(i)$ are obtained, consisting at most of N elements (FIG. 5). Lumen-intima interface 11 is therefore obtained from the interpolation of a set $\alpha$ of points $P_1(i)$. Similarly, the media-adventitia interface is obtained by interpolation of a set $\beta$ of points $P_2(i)$. This interpolation can be, for example, a linear interpolation, or a partial linear interpolation or an interpolation of an order higher than the first order.

As shown in FIG. 4, once the lumen-intima and media-adventitia interfaces are defined, it is possible to calculate the intima+media thickness s as a distance between the two interfaces. The algorithm used for calculating the intima+media thickness of vessel 1 depends, in general, on the type of interpolation used in the calculus of interfaces 11 and 12.

The detection of the lumen-intima interface can be made at two regions of interest 20 and 20' arranged on opposite sides of the cross section of vessel 1. This can be done to calculate the inner diameter $\Phi_i$ of vessel 1 that coincides with the distance between two diametrically opposite lumen-intima interfaces 11 and 11'.

An apparatus 100 for automatic detection of lumen-intima and media-adventitia interfaces in a blood vessel 1, as above described and illustrated, can be made as a modulus integrated in a new ultrasonographic machine, or as a retro-fit device that can be connected to an existing ultrasonographic machine, or still can be an electronic board to be plugged in an ultrasonographic machine.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realize the different functions described herein could have a different nature without, for this reason, departing from the field of the invention. It is to be understood that the phraseology or terminology employed herein is for the purpose of description and not of limitation.

What is claimed is:

1. An apparatus configured to detect lumen-intima and media-adventitia interfaces in a blood vessel comprising:

a means for aquiring a two-dimensional cross-sectional representation of said blood vessel, said two-dimensional representation being obtained as a grey level image, said acquisition means arranged to define in said image a region of interest (ROI) which includes said lumen-intima interface and said media-adventitia interface of said vessel, said region of interest consisting of a grey level map f(n, m) of said representation, being n and m coordinates of each pixel of said two-dimensional representation, a means for executing, along a search path (i) (with i=1 ... N) in said region of interest that is substantially orthogonal to a wall of said vessel where the following operations are executed:
detection of any discontinuity points by means of filtering said values f(n, m) along said path (i) and localization of said points,
definition along said path of a first discontinuity point $P_1(i)$ having contrast greater or equal to a first reference value $S_1$, and definition of a second discontinuity point $P_2(i)$ having contrast greater or equal to a second reference value $S_2$,
repeating the acquisition, filtering and definition operations for a number N of rectilinear search paths (i) in the above described region of interest (ROI):
detection of said lumen-intima interface by means of interpolation of a set α of said points $P_1(i)$ of the different search paths (i),
detection of said media-adventitia interface by means of interpolation of a set β of said points $P_2(i)$ of the different search paths (i),
wherein said step of detection of said discontinuity points $P_1(i)$ and $P_2(i)$ provides an operation selected from the group consisting of:
defining local peaks of a first order absolute central moment operator calculated as:

$$e(n, m) = \sum_{(k_2, l_2) \in \Theta_2} \left| \left[ \sum_{(k_1, l_1) \in \Theta_1} f(n - k_1, m - l_1) w(k_1, l_1, r_1) \right] - f(n - k_2, m - l_2) \right| w(k_2, l_2, r_2)$$

being $\Theta_1$ and $\Theta_2$ two circular domains having radius $r_1$ and $r_2$ respectively, defined as:

$$\Theta i = \{(k_i, l_i) \in Z^2 : \sqrt{k_i^2 + l_i^2} \leq r_i\},$$

where Z represents a set of whole numbers and $(k_i, l_i)$ are coordinates of a generic point with respect to a Cartesian plane with origin at (n, m), and wherein $w(k_1, l_1, r_1)$ is a weight function with unitary summation on a domain $\Theta_1$ and $w(k_2, l_2, r_2)$ is a weight function with unitary summation on a domain $\Theta_2$,
defining local peaks of a gradient of Gaussian operator calculated as:

$$G(n, m) = \sqrt{\left(\sum_{(k,l) \in \Theta} f(n-k, m-l) \cdot g_x(k, l)\right)^2 + \left(\sum_{(k,l) \in \Theta} f(n-k, m-l) \cdot g_y(k, l)\right)^2}$$

where $g_x(k, l)$ and $g_y(k, l)$ are derivatives of a Gaussian function with respect to directions x and y,
defining zero crossings of a Laplacian of Gaussian operator calculated as:

$$L(n, m) = \sum_{(k,l) \in \Theta} f(n-k, m-l) \cdot (g_{xx}(k, l) + g_{yy}(k, l))$$

where $g_{xx}(k, l)$ and $g_{yy}(k, l)$ are second derivatives of a Gaussian function with respect to directions x and y.

2. Apparatus, according to claim 1, wherein said first discontinuity point $P_1(i)$ corresponds to a discontinuity point nearest to a blood vessel center having contrast greater or equal to said reference value $S_1$, said second discontinuity point $P_2(i)$ being obtained starting from said first discontinuity point $P_1(i)$ proceeding outwards of said vessel along a relative search path (i).

3. Apparatus, according to claim 1, wherein said region of interest (ROI) is a rectangular matrix comprising R lines and C columns containing the values f(n, m) of the two-dimensional representation.

4. Apparatus, according to claim 1, wherein said two-dimensional representation is selected from the group comprised of:
a B-mode representation obtained by a sonographic apparatus,
a set of envelope curves of radiofrequency (RF) signals of a sonographic apparatus.

5. Apparatus, according to claim 1, wherein said contrast of said discontinuity point coincides with a value of an absolute central moment of the first order calculated in said point.

6. Apparatus, according to claim 1, wherein said contrast of said discontinuity point coincides with a value of said gradient of Gaussian calculated in said point.

7. Apparatus, according to claim 1, wherein said contrast of said discontinuity point coincides with a value of a slope of a zero crossing in said point.

8. Apparatus, according to claim 1, wherein said values of reference $S_1$ and $S_2$ are calculated for each search path (i) respectively as:

$$S_1 = TH_1 \cdot C_{MAX} \text{ and } S_2 = TH_2 \cdot C_1,$$

where
$C_{MAX}$ is a maximum of a contrast value of a discontinuity point of the i search path,
$C_1$ is the contrast value at point $P_1(i)$,
$TH_1$ is a constant having value comprised between 0 and 1 and $TH_2$ is a constant having value equal to 1.

9. Apparatus, according to claim 1, wherein furthermore, a step is provided of rejecting points $P_1(i)$ to which no points $P_2(i)$ correspond.

10. Apparatus, according to claim 1, wherein, furthermore, the operations are provided of:
measuring a distance of points $P_1(i)$ belonging to a set α taken from a calculated lumen-intima interface,
rejecting certain points $P_1(i)$ of those points having a distance, from said lumen-intima calculated interface, greater than a determined constant (DLI) forming a new set α' of points $P_1(i)$,
defining said lumen-intima interface by means of interpolation of said new set α',
iteration of the previous steps up to eliminating possible further points $P_1(i)$ of said new set α' having a distance, from said lumen-intima calculated interface, greater than DLI.

11. Apparatus, according to claim 1, wherein, furthermore, the following operations are provided:
measuring a distance of points $P_2(i)$ belonging to a set β taken from a calculated media-adventitia interface,
rejecting certain points $P_2(i)$ of those points having a distance, from said media-adventitia calculated interface, greater than a constant (DMA), forming a new set β' of points $P_2(i)$,
defining said media-adventitia interface by means of interpolation of said new set of points $P_2(i)$,
iteration of the previous steps up to eliminating further possible points $P_2(i)$ having a distance, from said media-adventitia calculated interface, greater than DMA.

12. Apparatus, according to claim 1, wherein said interpolation of said set α of said points $P_1(i)$ and said interpolation of said set β of said points $P_2(i)$ is selected from a group consisting of:
 linear interpolation,
 linear partial interpolation, and
 interpolation of order higher than a first order.

13. Apparatus, according to claim 1, wherein an intima+media thickness is calculated as a succession of two-dimensional representations corresponding to one or more cardiac cycles, whereby it is possible to monitor its variation during such cardiac cycles.

14. Apparatus, according to claim 1, wherein a diameter of said vessel is calculated as a succession of two-dimensional representations corresponding to one or more cardiac cycles of a distance between said lumen-intima interface and said media-adventitia interface at two opposite sides of said cross section of said vessel.

15. Ultrasonographic machine comprising an apparatus configured to detect of lumen-intima and media-adventitia interfaces in a blood vessel according to claim 1.

* * * * *